United States Patent [19]

Hillel et al.

[11] Patent Number: 4,496,351
[45] Date of Patent: Jan. 29, 1985

[54] INFUSION MONITOR

[75] Inventors: Arie Hillel, White Plains, N.Y.;
Simcha Borovsky, Givatayim, Israel

[73] Assignee: Ipco Corporation, White Plains, N.Y.

[21] Appl. No.: 502,585

[22] Filed: Jun. 9, 1983

Related U.S. Application Data

[63] Continuation-in-part of Ser. No. 365,595, Apr. 5, 1982, abandoned.

[51] Int. Cl.³ ............................................. A61M 5/16
[52] U.S. Cl. .................................. 604/250; 604/253; 604/65; 128/DIG. 13
[58] Field of Search ........... 128/DIG. 13 X; 604/250, 604/253, 256, 65

[56] References Cited

U.S. PATENT DOCUMENTS

| | | | |
|---|---|---|---|
| D. 250,085 | 10/1978 | Tuttle | 604/250 X |
| 3,563,090 | 2/1971 | Deltour | 604/253 X |
| 4,137,940 | 2/1979 | Faisandier | 604/253 X |
| 4,314,567 | 2/1982 | Cannon | 128/DIG. 13 X |
| 4,346,606 | 8/1982 | Cannon et al. | 604/253 X |
| 4,397,648 | 8/1983 | Knute | 604/253 |
| 4,410,164 | 10/1983 | Kamen | 604/250 X |

Primary Examiner—Edward M. Coven
Attorney, Agent, or Firm—Stoll, Wilkie, Previto & Hoffman

[57] ABSTRACT

An infusion monitor for feeding liquids to patients which is light weight so that it may be easily hung on a liquid dripper and which is provided with means for pre-setting the volume infused and the rate of infusion. Means are also provided for automatically varying the rate of infusion, for automatically cutting-off the infusion and for sounding an alarm to alert an attendant if any variation from pre-set limits occur.

7 Claims, 16 Drawing Figures

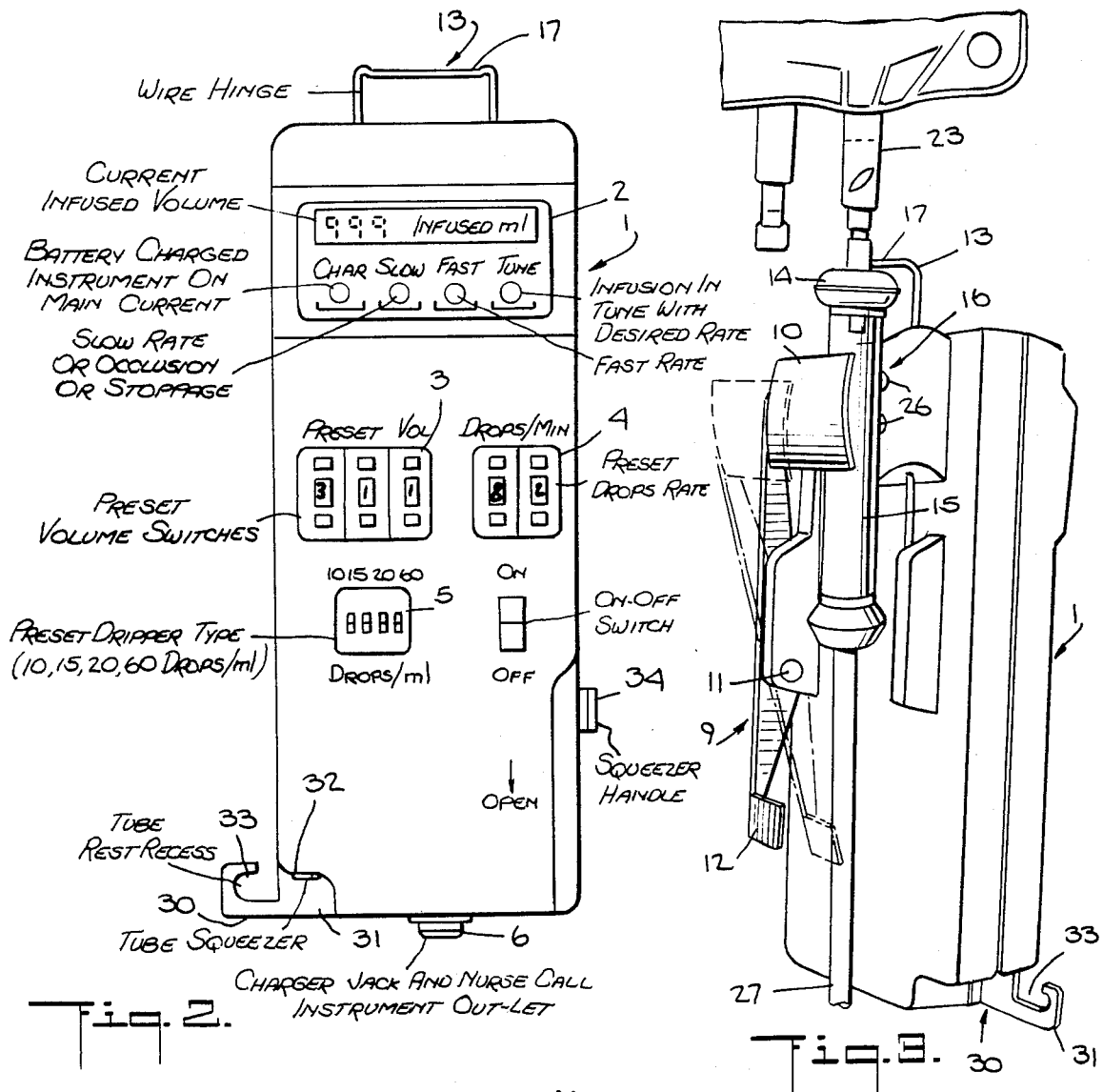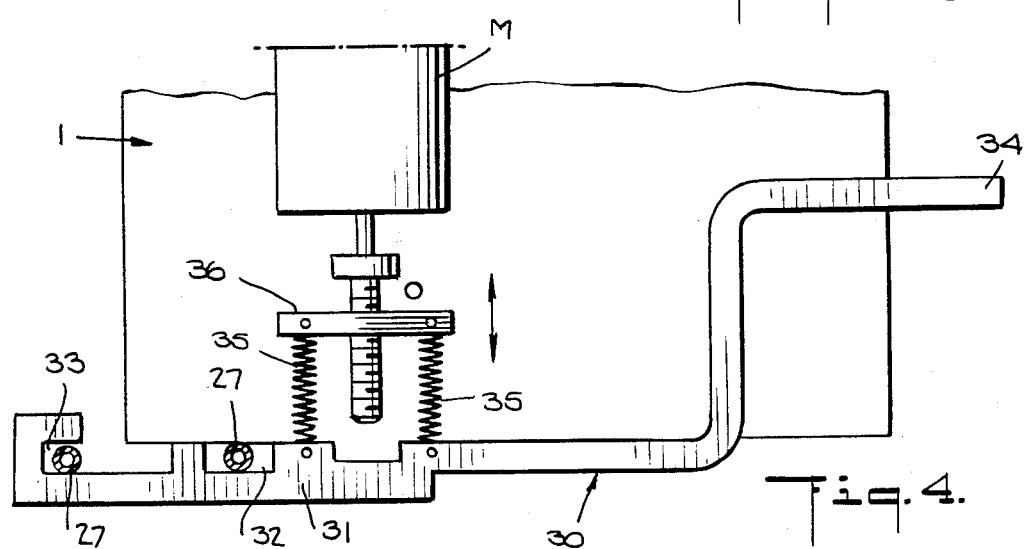

Fig.6B.

INFUSION MONITOR

RELATED APPLICATION

This application is a continuation-in-part of U.S. patent application Ser. No. 365,595 filed Apr. 5, 1982, now abandoned.

BACKGROUND OF THE INVENTION

Intravenous liquid infusion means for infusing patients with food, blood, drugs, and the like are used in numerous medical applications. Infusion monitors usually comprise a suitable reservoir for the solution to be infused which is connected to a dripper and from which extends a feed tube leading to an intravenous needle for injection at the venipuncture point of the patient. A tube clamp is normally placed along the feed tube to control the flow of the liquid being infused. The proper and reliable control of the rate and volume of infusing these liquids is essential to patient management and recovery. Proper infusion rates and volume may vary from a few cubic centimeters per hour to several cubic centimeters per minute. Hence, it is extremely important that the infusion rate and volume be accurately and continuously monitored and controlled.

Heretofore, the methods employed for monitoring and controlling the rate and volume of infusion have been time-consuming and of limited accuracy. Typically, an attendant sets the flow rate by counting the drops per minute from the reservoir. The rate is thus determined slowly, with difficulty and with little accuracy. Because of the heavy pressure on the attendant's time, there is usually little or no correction for any variations in the flow rate or for clearing of any blockage of the needle by clotting, etc. Such blockages can be dangerous to the patient if not readily noted and require time-consuming and painful needle replacement to re-establish flow. Similar difficulties arise when an empty bottle goes unnoticed.

In the prior art there are also provided infusion monitoring systems which monitor the amounts infused by using electro-optical sensing means. However, in such systems, the cartridge and sensing systems are quite complicated and are connected to the feeding assembly by complicated clamping means. This requires complex alignments of the optical sensing system and more complex monitoring devices.

In some prior monitors of the prior art, the optical sensing system is on both sides of the dripper tube, i.e. the emitter and the receiver are diagonally across from each other with the dripper tube therebetween. This necessitates positioning of the electrical or other controls on both sides of the tube which increases the size and weight of the monitor.

In such units, alignment of the emitter and receiver with the dripper tube properly and accurately aligned therebetween is essential in order for the optical sensing means to sense the liquid drops. Any disturbance in this alignment tends to give false readings.

Furthermore, is existing monitors, it has been noted that the tube squeezing mechanisms in use have a tendency to permanently distort the feeder tube when the tube is being squeezed so that when pressure on the feeder tube is relaxed, a permanent crimp sometimes remains in the feeder tube thus restricting the flow of fluid when such restriction is neither needed nor desired.

SUMMARY OF THE INVENTION

The present invention avoids the above difficulties and has for one of its objects an improved infusion monitor which will automatically and continuously monitor and adjust the desired flow rate.

Another object of the present invention is the provision of an improved infusion monitor which is light and simple so that it may be hung directly from the dripper tube.

Another object of the present invention is the provision of an improved infusion monitor which will continuously indicate the amount of fluids infused into the patient.

Another object of the present invention is the provision of an improved infusion monitor which may be pre-set to shut-off the flow when the desired volume has been administered.

Another object of the present invention is the provision of an improved infusion monitor which is provided with warning devices which give signals at the patient's side and/or at the nurse's desk so that the attendant is alerted to any variation or stoppage of the pre-set infusion rate.

Another object of the present invention is the provision of an improved monitor in which the optical sensing mechanism is on one side of the dripper tube.

Another object of the present invention is the provision of an improved monitor in which the emitter and receiver of the optical sensing mechanism is on the same side of the dripper tube.

Another object of the present invention is the provision of an improved monitor in which reflecting means are provided for said optical sensing mechanism to reflect the sensing beam for the emitter to the receiver.

Another object of the present invention is the provision of an improved monitor in which the reflecting means are part of the clamping means.

Another object of the present invention is the provision of an improved monitor in which means are provided for automatically aligning the dripper with the optical sensing means.

Another object of the present invention is the provision of an improved monitor in which means are provided to virtually eliminate permanent crimping of the feeder tube.

Another object of the present invention is the provision of an improved monitor which preferably uses a feeder tube squeezing mechanism which virtually eliminates permanent crimping of the feed tube.

Other and further objects of the invention will be obvious upon an understanding of the illustrative embodiment about to be described, or will be indicated in the appended claims, and various advantages not referred to herein will occur to one skilled in the art upon employment of the invention in practice.

In accordance with the present invention, the instrument incorporates an electro-optical device which senses the drop rate and counts the number of drops infused. By pre-setting the unit to a predetermined number of drops per cubic centimeter, the number of drops counted by the optical system are translated to volume infused. This volume is continuously displayed on the instrument. A plastic feed tube leads from the dripper to the infusion needle and is attached to a squeezing mechanism operated by a motor in the instrument which automatically squeezes or releases the feed tube.

By pre-setting the desired drip rate, the squeezer will automatically squeeze or release the tube to tune the tube to allow the desired rate of drip only to be infused. The instrument may also be pre-set to the amount of liquid to be infused so that when the desired volume is reached, the instrument will command the squeezer to completely squeeze the tube and cut-off the flow. Fast and slow alarms, alerted by both light and sound, may be provided and a continuous alarm may also be provided to constantly alert the attendant when the flow is continuous, the bag is empty, or there is an electrical failure. This same information may be transmitted to the attendant's desk or to any other alert system.

The cartridge of the present invention is of such light weight that, together with the entire circuitry and the battery included therein, it may be hung from the dripper tube directly. Hence, the drops passing from the dripper tube may be sensed by the electro-optical sensing system of the present invention. This may be done without complicated clamping and sensing devices.

The cartridge of the present invention provides an electro-optical sensing system in which the emitter and the receiver are on the same side of the cartridge and in which reflecting means are used to reflect the beam from the emitter back to the receiver. Preferably, the reflecting means is part of the means for clamping the monitor cartridge on the dripper tube. With this structure, the entire circuitry and electronics of the monitor is located on one side of the dripper tube so that the cartridge for the monitor can be made compact and light weight. Since the clamping mechanism is provided with the reflecting means and it is opposite the sensing means, the operator is assured that as soon as the cartridge is clamped onto the dripper tube, the electro-sensing and reflecting means are immediately in alignment with each other as well as in alignment with the dripper tube so that there is no danger of misalignment.

Furthermore, the present invention preferably utilizes a tube-squeezing mechanism which minimizes, if not eliminates, any permanent crimping of the feeder tube so that when pressure on the feeder tube is released, the feeder tube returns substantially to its original configuration.

BRIEF DESCRIPTION OF THE DRAWINGS

A preferred embodiment of the invention has been chosen for purposes of illustration and description and is shown in the accompanying drawings forming a part of the specification, wherein:

FIG. 2 is a front view of the cartridge of the present invention.

FIG. 3 is a rear view showing the unit in its operative position.

FIG. 4 is a fragmentary plan view showing the automatic tube squeezer mechanism.

FIGS. 6A and 6B are diagrammatic views showing the circuit in greater detail.

DETAILED DESCRIPTION OF THE INVENTION

Figure 1:
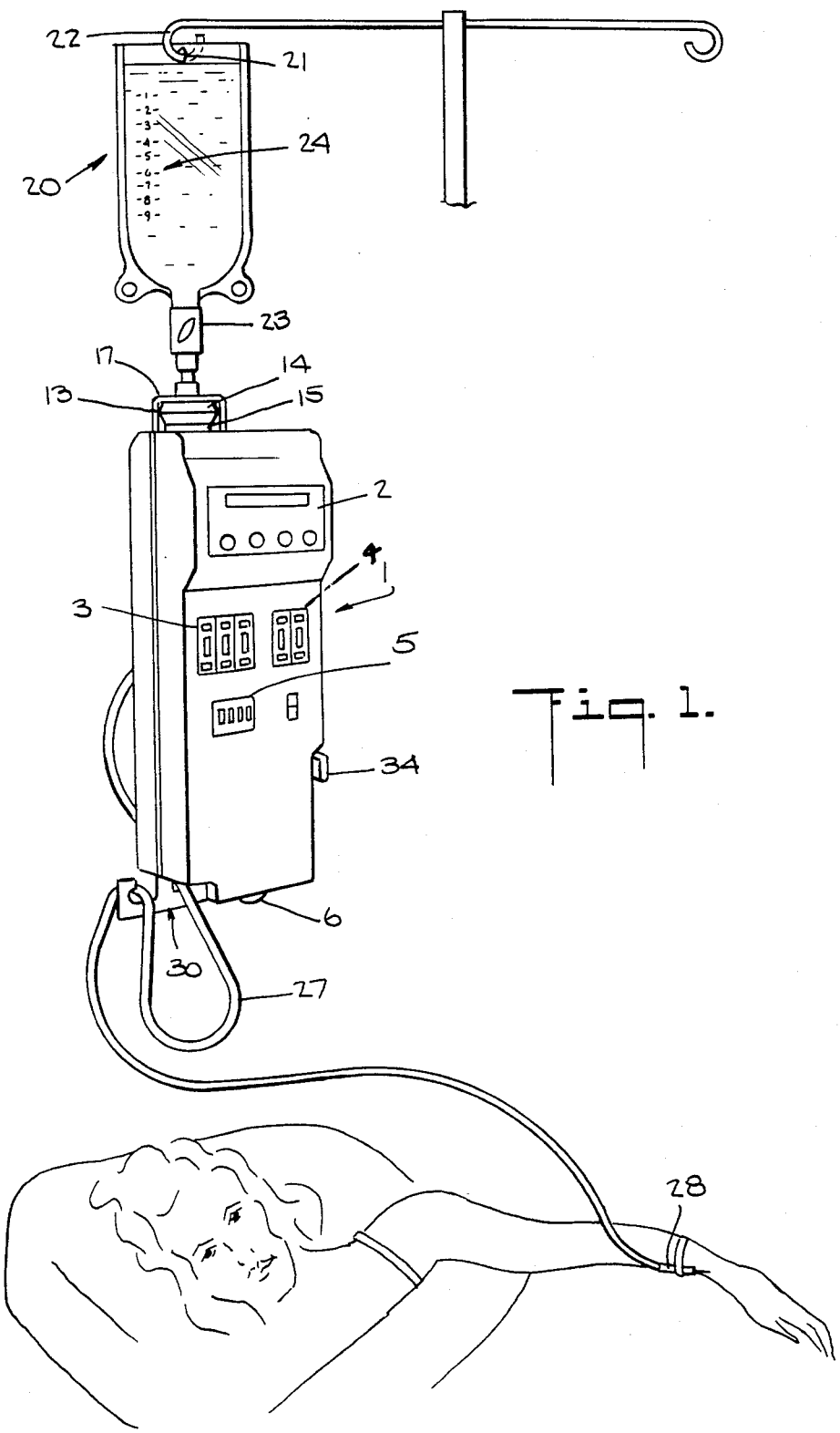
FIG. 1 is a perspective view showing the fusion monitor of the present invention in use and feeding a patient.

Referring more particularly to the drawings and particularly to FIGS. 1 to 4, the improved infusion monitor of the present invention comprises an outer cartridge 1 within which the circuitry and battery is packaged. The infusion liquid is usually stored in a transparent container 20 which may be a rigid or flexible container and may be made of a glass or plastic material. The container 20 is provided with a hanging opening 21 at the top from which it may hang on a hook 22 of an I. V. stand and has an outlet tube 23 at the bottom. Visual measuring indicia 24 may also be provided on the container 20 to give the attendant a visual indication of the amount of fluid remaining therein.

A dripper assembly 15 is inserted in the outlet tube 23. The dripper 15 is provided with an upper flange 14 at its top and is adapted to have a hollow feed tube 27 attached to the bottom thereof. The dripper 15 is a hollow structure preferably made of a transparent plastic or glass material, as is usual in such products. The feeder tube 27 has an intravenous needle 28 attached thereto at its lower end which is adapted to be inserted into the patient for feeding the patient. When the patient is to be infused with a liquid, the attendant sets the cartridge 1 for the rate, volume and type of drip desired (as will be described in greater detail hereinbelow) and the infusion process starts. Display devices 2 are provided in the cartridge 1 to indicate amounts infused as well as to indicate whether the battery is charged and whether the rate of infusion is slow, fast or in tune as will be described in greater detail hereinbelow. The cartridge is also provided with a plurality of switch assemblies 3, 4 and 5 which may be used to pre-set the desired volume, the desired rate and the desired drip-type. The number of drops per CC is pre-set as indicated on the dripper, so that the number of drops counted is translated into infused volume. A charger jack and nurse call instrument outlet 6 may also be provided.

The rear of the cartridge 1 is provided with a clamping assembly in the form of a two-arm lever 9 which is pivotally mounted thereto at pivot 11. The clamping assembly 9 has a clamp 10 at the end of its upper arm and a mirror handle 12, which is used to open and close the clamp 10, at the end of its lower arm. A wire hinge 13 is provided which has an arcuate portion 17 which is adapted to rest on the upper dripper flange 14 of the dripper 15. The dripper tube 15 is adapted to lie in a concave seating surface 16 at the rear of the cartridge 1 and is held in place by the spring-pressed clamp 10. It will be seen from this structure that the cooperation between the wire hinge 13 and the clamp 10 together with the seating surface 16 permits the cartridge 1 to be quickly and easily mounted onto the dripper 15. The flange 14 of the dripper 15 extends above the top edge of the cartridge 1 and the hinge 13 hangs over and rests on the flange 14 so that when the clamp 10 applies pressure to the dripper 15, it will be held tightly within and against the seating surface 16 of the cartridge 1. Hence, the cartridge 1 may be very quickly and easily assembled onto the dripper 15 and may be just as easily disassembled therefrom.

The concave holder 16 is provided with a pair of vertically oriented aligned optical sensing openings 26 which permit sensing beams from the sensing means to pass therethrough. These sensing beams sense the liquid drops as they pass down the dripper tube 15 and are thus able to count the number of drops and determine the rate of infusion. A flexible feed tube 27 leads from the dripper 15 and is adapted to be squeezed to restrict its inner passageway so that the amount of fluid infused is decreased or stopped altogether, and, alternately, the squeezing action of tube 27 may be released to open its inner passageway and allow a greater amount of liquid to be infused.

Figures 3A, 3B, 3C:
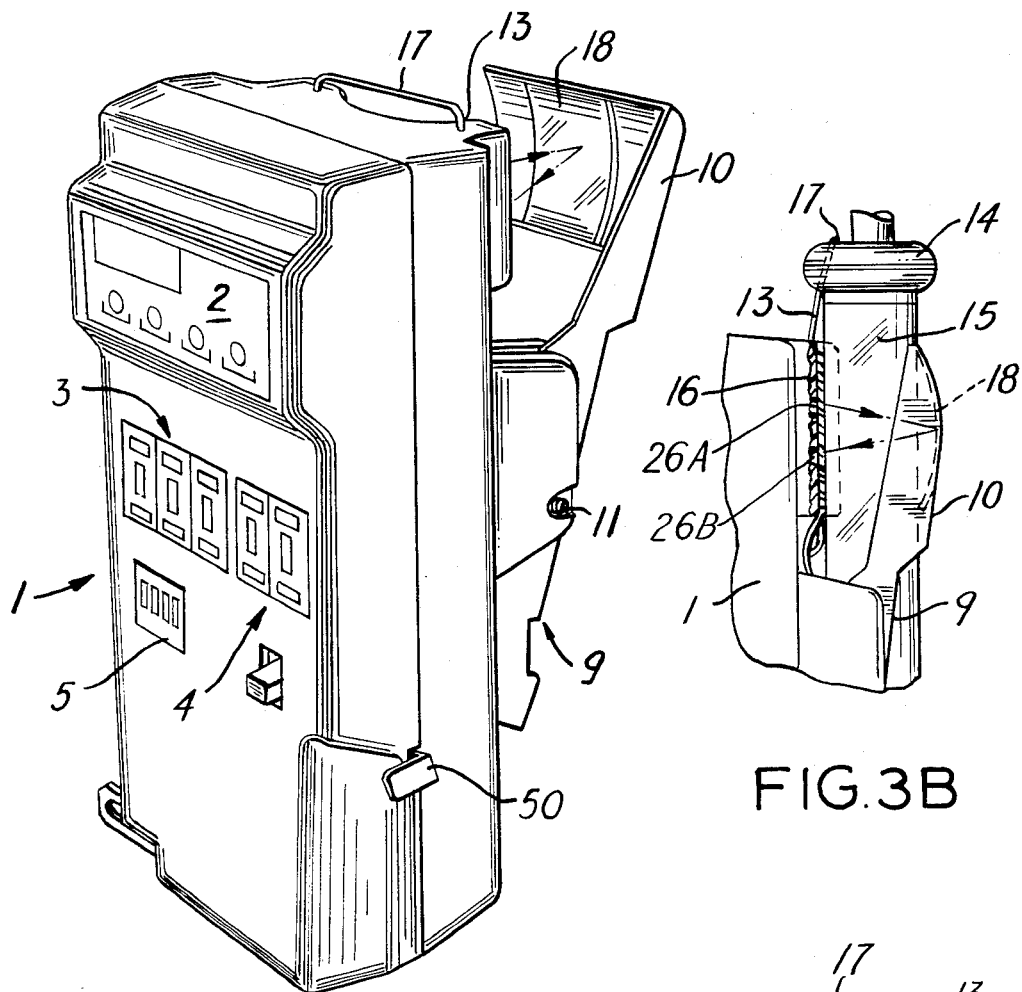
FIG. 3A is a perspective view of the front portion of the cartridge.
FIG. 3B is a detail partly in section showing the optical-sensing and reflecting mechanism of the present invention.
FIG. 3C is a partial plan view of the openings for the optical-sensing mechanism of the present invention.
Figure 3D:
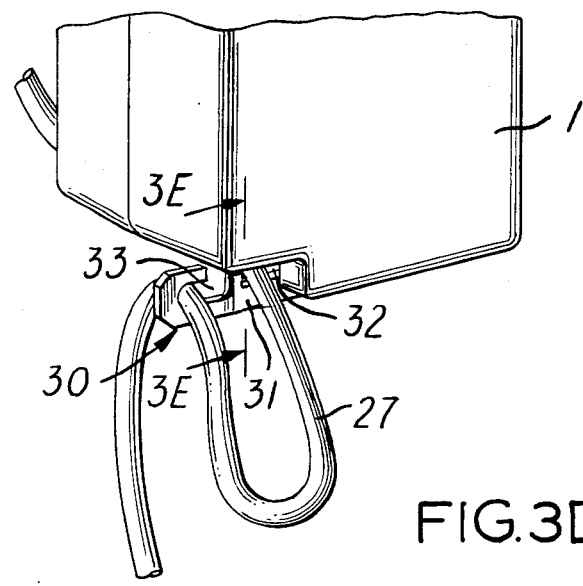
FIG. 3D is a fragmentary perspective view of the tube-squeezing mechanism preferably used with the present invention.
Figure 6A:
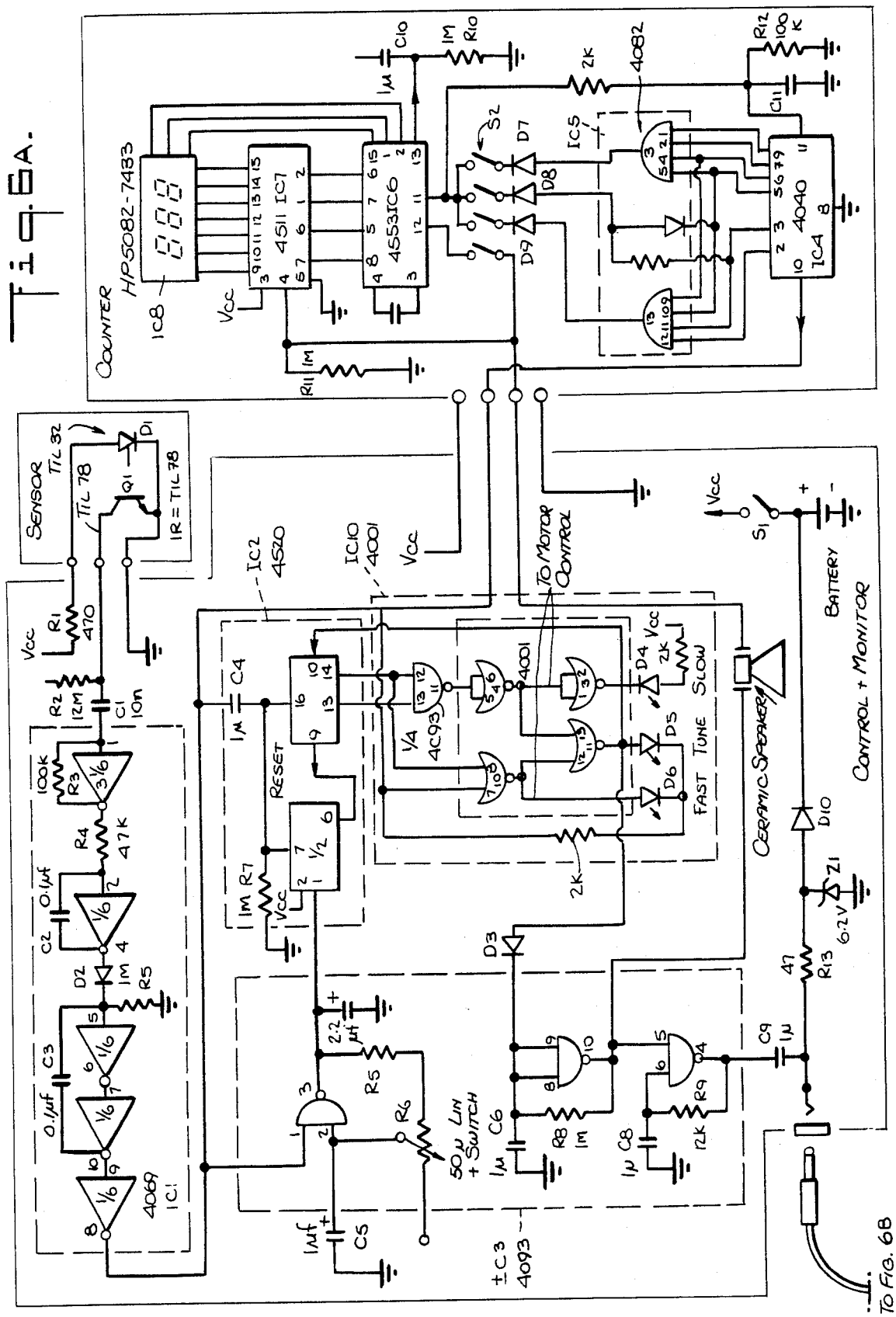
Figure 6B:
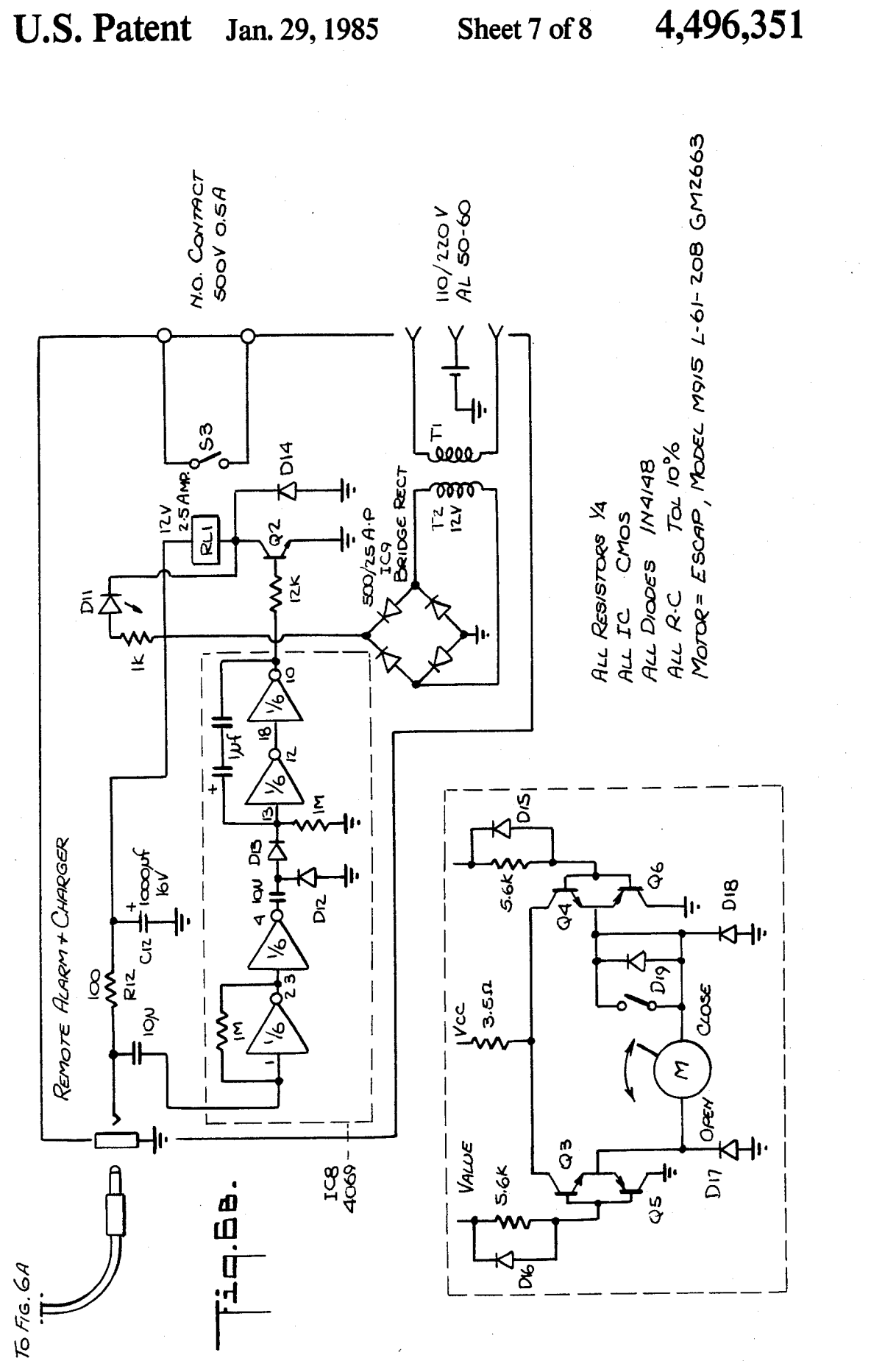

Referring more particularly to FIGS. 3A to 3C, the optical-sensing mechanism 26 of the present invention is shown in greater detail. The optical emitter and the receiver D1-Q1 (FIG. 6A) are located in the arcuate portion 16 of the cartridge 1 and are shown as preferably being vertically oriented with respect to each other. The emitter sensing pulse leaves the cartridge 1 through opening 26A and the receiver detects the sensing pulse through the opening 26B, as shown in broken lines in FIG. 3B. The clamp 10 of the clamping assembly 9 has a reflecting surface 18, which may be an arcuate mirror, opposite the openings 26A and 26B. The mirror 18 is shaped so that the sensing pulse from the emitter opening 26A is reflected back by the reflecting surface 50 to the receiver through opening 26B. This insures that when the clamp 10 is firmly holding the cartridge 1 on the dripper 15, as shown in FIG. 3B, the operator knows that the monitor is in place and in perfect alignment to automatically monitor the drops falling through the dripper 15. With this structure and because the clamp 10 holds the dripper 15 snugly in concave seating portion 16, the operator is assured that once the cartridge 1 is mounted on the dripper 15, no further adjustments or alignments are necessary. Furthermore, even if the cartridge 1 rotates on the dripper 15 or is somehow disturbed, the spring-pressed clamp 10 will automatically move it back into the aligned position within concave portion 16 so that the danger of the cartridge becoming misaligned is virtually eliminated.

An automatic squeezing assembly 30 is provided in the cartridge 1 to automatically apply or release pressure on the feed tube 27 to restrict or enlarge its inner passageway. The squeezing assembly 30 comprises an arm 31 having a squeeze notch 32 and rest notch 33 at one end and has a handle 34 at its other end. The arm 30 is connected by a downwardly biased spring 35 to a bracket 36 which is operatively connected to a motor M and which is adapted to raise or lower the squeezing assembly 30. When the motot M is commanded to raise the squeezing assembly 30, the tube 27 is squeezed between the squeeze notch 32 and underside of the cartridge 1 to restrict the passageway of the feed tube 27. When the motor M is commanded to lower the squeezing assembly 30, the pressure on the tube 27 is released so that its passageway is enlarged to permit a greater amount of fluid to be infused. As will be described hereinafter, the motor M may be commanded to squeeze the feed tube 27 to completely stop the flow of liquid. Before the feeding operation is started, the feeding tube 37 is inserted not only in the feeder notch 31 but is also looped around rest notch 33 to prevent the tube 27 from hanging loose and restricting its passageway by its own weight.

Referring now to FIGS. 3D through 3G, the squeezing notch 32 of the squeezing unit 31 preferably used with the present invention is more clearly described and claimed in the patent application Serial No. 502,586 of Arie Hillel filed contemporaneously herewith and copending herewith. That application discloses and claims a squeezing edge so structured so as to minimize the amount of permanent crimping of the feed tube 27. As seen from the cross-sectional view of FIG. 3G, the squeezing means 40 of the squeeze notch portion 32 of the squeezing unit 31 comprises a pair of opposed flat substantially parallel side walls 41 and 42 and an inwardly angled wall portion 43 extending from one side wall 43 and terminating in a flattened upper squeezing edge 44. Preferably, the ratio of the angled portion 43 to the flattened upper squeezing edge 44 is 6 to 1, the angled portion 43 is at about a 30° angle to the vertical, the angled portion 43 is approximately 1.2 millimeters deep and the flattened squeezing edge portion 44 is approximately 0.2 millimeters wide.

Figure 3E:
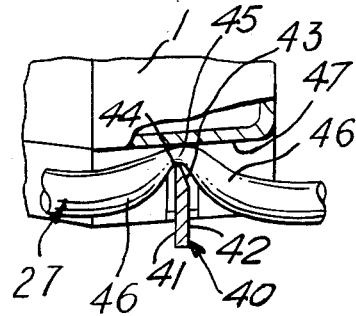
FIG. 3E is a sectional view taken along line 3E—3E of FIG. 3D showing the feeder tube being squeezed.
Figure 3F:
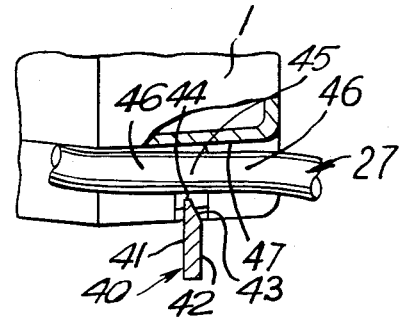
FIG. 3F is a sectional view similar to FIG. 3E showing the feeder tube after pressure has been released therefrom.
Figure 3G:
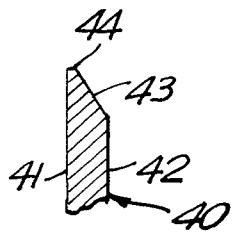
FIG. 3G is an enlarged sectional view of the edge of the preferred squeezing mechanism.

With this preferred structure and as further explained in said contemporaneously filed patent application, when the feed tube 27 is squeezed by the squeezing edge 44 against lower flat wall 47 of the cartridge, as shown in FIG. 3E, the tube area 45 squeezed by the squeezing edge 44 is so small as compared to the rest of the tube 27 that the portions 46 of the tube 27 immediately adjacent the squeezed area 45 are not permanently distorted by the pressure of the squeeze edge 44. Thus, when pressure on the feed tube 27 is released, as shown in FIG. 3F, the portions 46 adjacent the squeezed area 46 of the feed tube 27 are resilient enough to move the squeezed area 45 of the feeder tube 27 outwardly substantially to its original configuration so that virtually no permanent crimping results from squeezing of the feed tube 27. Hence, the operator knows that when pressure on the feed tube 27 is released, substantially the entire inner diameter of the feed tube 27 is open for fluid to flow through.

Figure 4A:
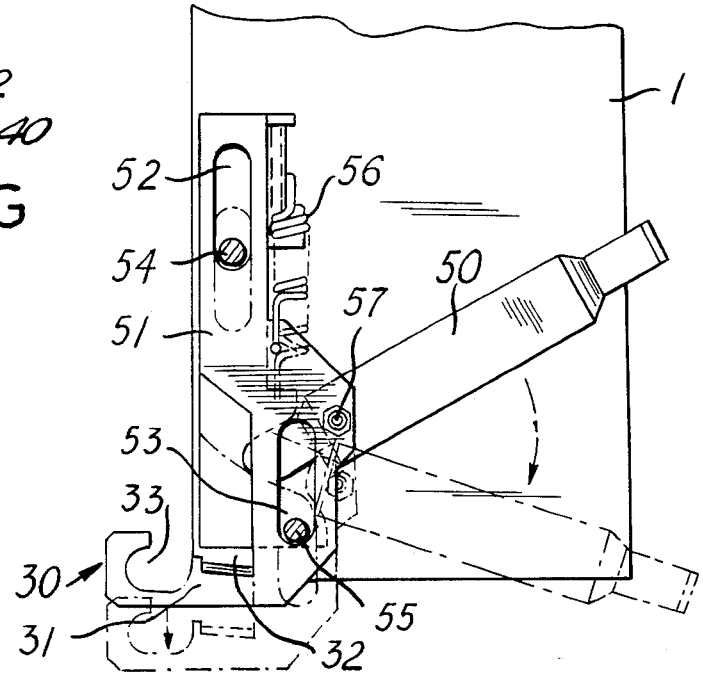
FIG. 4A is a schematic elevational view showing an alternate means for raising and lowering the tube-squeezing mechanism.
Figure 5:
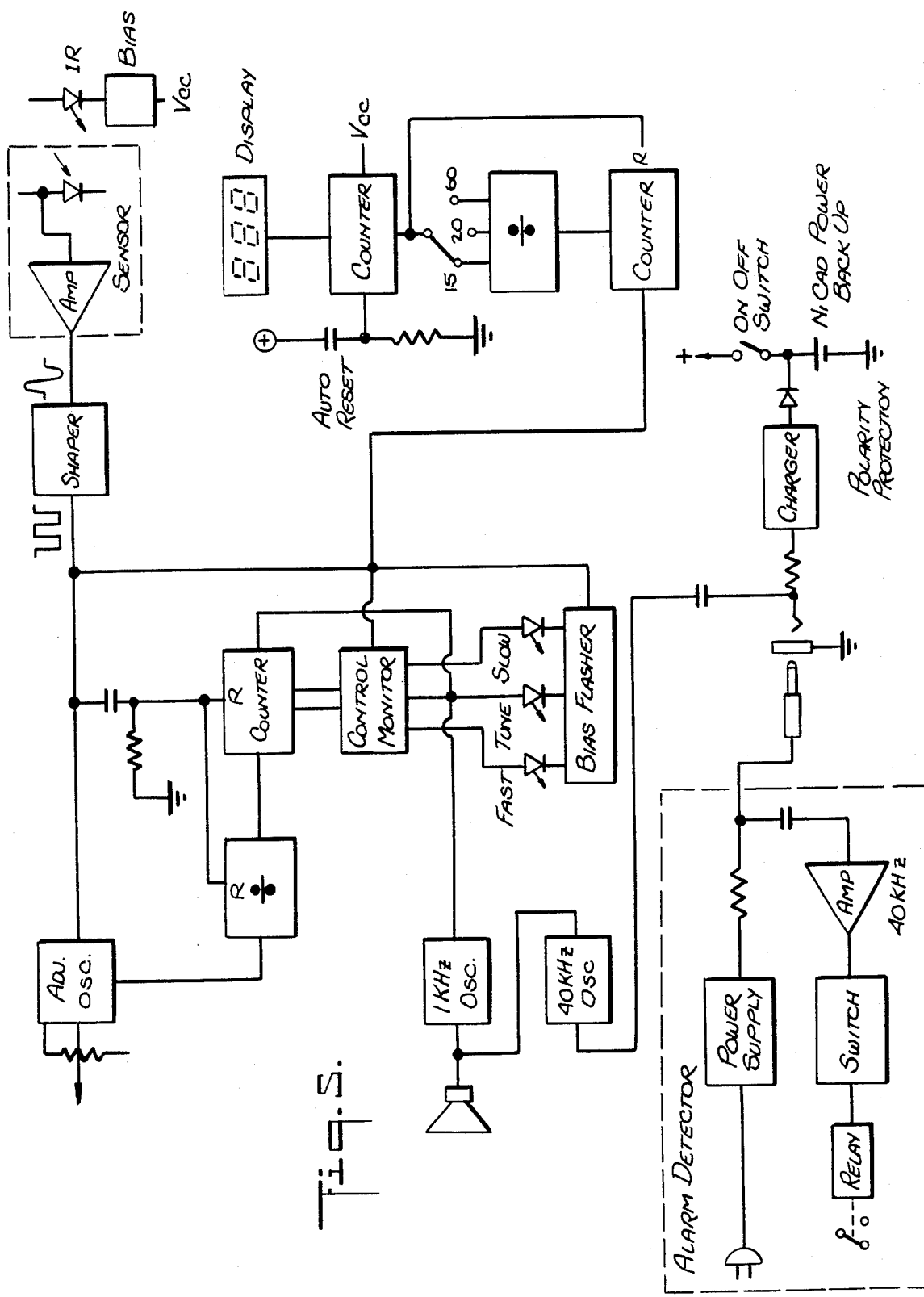
FIG. 5 is a diagrammatic block view showing the circuit used with the present invention.

Referring now to FIG. 4A, an alternate mechanism for manually moving the squeezing unit 31 away from the feed tube 27 is shown. In this embodiment, which is the preferred embodiment of the invention, a lever arm 50 is pivotly mounted to a 57 and extends from an upwardly vertical slide extension 51 of the squeezing unit 31. The vertical slide extension 51 has vertical parallel notches 52 and 53 in which are mounted pins 54 and 55, respectively, to keep the slide extension 51 in alignment. A spring 56 is mounted on the side extension 51 to bias the unit upwardly. When activated the motor M (not shown in FIG. 4A) moves the slide extension 51 down against the action of the spring 56. When the motor is deactivated and the downward pressure released, the spring 56 will automatically move the slide extension 51 upwardly. The lever arm 50 extends from the slide extension 51 in order to permit manual movement of the slide extension 51 and the squeezing assembly 31 against the action of the spring 56.

Referring now to FIGS. 5, 6A, 6B and 7, which show the details of the preferred circuitry used with the present invention, the power source and circuitry is preferably contained directly within the cartridge 1 so that it can be hung on the dripper. It derives power from a battery (which may have a charger unit) and it comprises diode D1 and transistor Q1 which are paired light emitting diode and photo transistors. The diode D1 is biased on so that the transistor Q1 is also on. When a drop drops through the dripper 15 passes between the diode D1 and the transistor Q1, the drop is sensed through the sensing openings 26 in the cartridge 1. As the drops pass by, the transistor Q1 is momentarily cut-off so that a negative-going pulse is generated. This negative-going pulse is coupled by capacitor C1 into pin 1 of IC1 which is a hex inverter. Five of the six inverters on this chip (4069) are used to shape the pulse into a negative-going square wave.

This negative square wave pulse appears at pin 8 of IC1 and is directly connected to pin 1 of IC3 which is a quad nand-schmidt trigger chip (CD4093). One stage of this chip with its output on pin 3 is used as an oscillator which is activated when the output of pin 8 of IC1 is high and which is cut-off when said pin 8 goes low. Therefore, the duration of an interrupted period of oscillation is the time between successive drops. The frequency of oscillation is controlled by resistor R6 which is a front panel activated potentiometer. The frequency of oscillation and the duration will control the number of counts that will be performed by the counter IC2 (CD4520).

The detection system of this invention is formed by IC2 and IC10, together with one section of IC3, and the LED's D4 through D6 which display lights on the front panel. The display lights 6 are marked "Slow", "tuned" and "fast". When the drip count is greater than that called for by the setting of potentiometer R6, the "fast" LED lights up. When the drip count corresponds to the number called for by the setting of R6, the "tune" LED lights up. When the drip count is slower than that called for by R6, the "slow" LED is activated.

The stage of IC3 with an output on pin 10 is an 1K oscillator which is activated to drive a speaker when the demanded count is not delivered and constitutes the warning signal. When the dripping stops, the oscillator goes on, and stays on, so that the alarm is constant until an attendant rectifies the situation. The output at pin 10 of IC3 also enables another oscillator whose output is on pin 4 of IC3 and is coupled by C9 to the DC power line. In conjunction with Q2 and RL1 of IC8 it closes switch S3 to enable an alarm in the nurses quarters.

Figure 7:
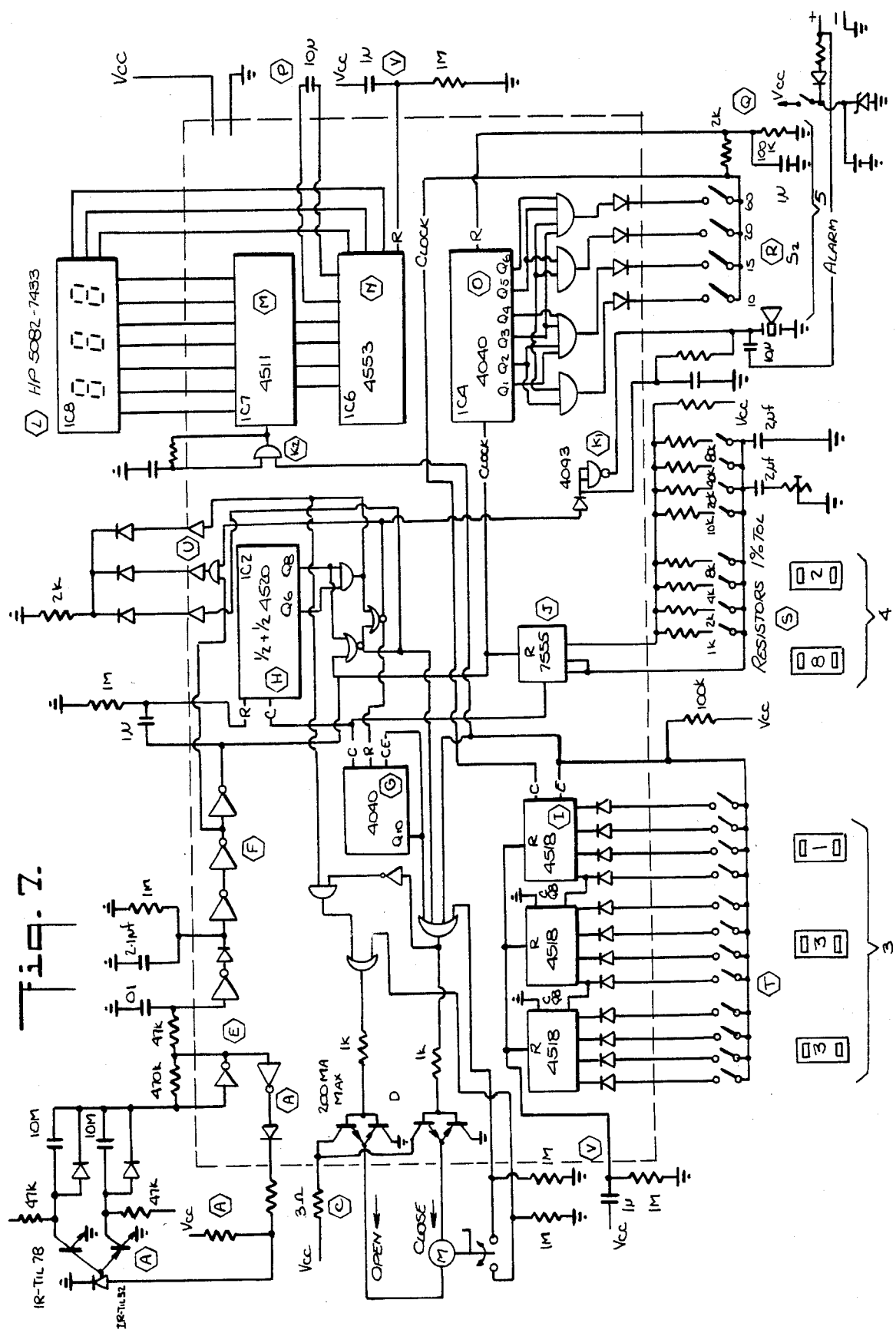
FIG. 7 is another diagrammatic view showing the circuit in still greater detail.

IC4 is a binary counter which counts the number of drops as indicated by the pulse from pin 8 of IC1. The output of IC4 is fed to IC5 which is a dual quad "and" gate, and to a set of three diodes D7 through D9. These diodes are connected to IC6 through a four position switch assembly S2, (S on FIG. 2), a single diode only of which can be accommodated at a time. One position of S2, which is not connected to the diodes, is used to turn on the audible alarm. The other three positions are used to choose which output should be connected to the input of IC6. The outputs of the two "and" gates and the direct output from IC4 are weighted. Each output corresponds to a given number of drips per CC. In this manner, the switch S2 can be set so that the reading on IC8 will indicate total accumulation of CC's delivered and the desired ratio of drops to CC. Likewise, the switches 3 and 4 are comprised of a plurality of sets of diodes and resistors, respectively, as shown in FIG. 7 may be used to pre-set the volume and to pre-set the drop rate. The number of drops per CC is pre-set as indicated on the dripper 15 so that the number of drops counted corresponds to infused volume.

The DC power supply/charge comprises T1, T2 and IC9 and filter capacitor C12. R12, R13 and 21 make up the regulating circuit, keeping the voltage at junction 21 and D10 to 6.2 V . D10 blocks any reverse current from the battery and also decreases another 0.7 V. The charging current is limited by R12 and R13.

The driving circuit for the motor "M" comprises transistors Q3 through Q6 and diodes D15 through D18 with their associated circuitry. The motor "M" is connected to the "Fast" and "Slow" circuitry of IC10 so that at a command from the "Fast" or "Slow" circuit the motor "M" is activated. The motor "M" is controlled by transistors Q3-Q5 or transistors Q4-Q6. When the "Fast" or "Slow" circuitry of IC10 indicates that the rate is not in tune, i.e. is either faster or slower than the pre-set rate, then the transistor assemblies Q3-Q5 or Q4-Q6 are activated in order to move the motor in one direction or the other so as to squeeze the feed tube 27 to restrict the flow, or to relax the feed tube 27 to increase the flow. This occurs until the amount infused is in tune, at which point there is no pulse from the "Fast"-"Slow" circuitry and the motor stops. As will be understood, if the rate is in tune as pre-set, then there is no pulse and the motor "M" remains inactive. Upon command from the CC measurement circuitry the motor will go its "Maximum squeeze" condition so that after a pre-set number of CC's have been delivered to the patient, flow is stopped entirely.

It will thus be seen that the present invention provides an improved infusion monitor which may be easily hung from the dripper which will automatically and continuously monitor and adjust the desired flow rate, which will continuously indicate the amount of fluid infused into the patient, which may be pre-set to control the flow infused or shut-off the flow when the desired volume has been administered, and which is provided with warning devices which give signals at the patient's side and/or at the nurse's desk so that the attendant is alerted to any variation or stoppage of the pre-set infusion rate.

It will further be seen that the present invention provides an improved monitor in which the optical-sensing mechanism is on one side of the dripper tube with the emitter and receiver thereof on the same side of the dripper tube and in which reflecting means are provided for the optical-sensing mechanism to reflect the sensing beam from the emitter to the receiver.

The present invention further provides a monitor in which the reflecting means are part of the cartridge clamping means to permit automatic alignment of the dripper with the optical-sensing means.

In addition, the present invention provides an improved monitor utilizing a preferred squeezing unit which virtually eliminates permanent crimping of the feeder tube and in particular such means comprise the configuration of the squeezing mechanism to virtually eliminate permanent crimping of the feed tube.

Although the present invention has been described with respect to an infusion monitor for feeding liquids to patients for medical purposes, it will be understood that this system may be used for monitoring the infusion of liquids for purposes other than medical purposes.

As many and varied modifications of the subject matter of this invention will become apparent to those skilled in the art from the detailed description given hereinabove, it will be understood that the present invention is limited only as provided in the claims appended hereto.

The embodiments of the invention in which an exclusive property or privilege is claimed are defined as follows:

1. An infusion monitor comprising a cartridge, sensing means operatively associated with said cartridge for monitoring the flow of liquid in a transparent infusion tube assembly, said sensing means comprising a sensing beam for sensing a liquid being infused through said transparent infusion tube assembly, means for directing said sensing beam from said cartridge, a movable clamp assembly pivotly mounted on said cartridge, reflecting means on said clamp assembly for re-directing said sensing beam back toward said cartridge, said cartridge having openings therein for said sensing beam, said reflecting means being opposite said openings, an emitter and a receiver for said sensing beam within said cartridge adjacent said openings, said clamp assembly being movable relative to said openings to reflect said beam and to permit the cartridge to be mounted on said infusion tube assembly and support said cartridge on said infusion tube assembly.

2. A monitor as claimed in claim 1 wherein said cartridge has an arcuate seating portion and wherein said openings are located in said seating portion.

3. A monitor as claimed in claim 2 wherein said openings are adjacent to each other.

4. A monitor as claimed in claim 3 wherein said openings are vertically oriented with respect to each other.

5. A monitor as claimed in claim 4 wherein said reflecting means is an arcuate reflecting means.

6. A monitor as claimed in claim 5 wherein said openings are adjacent an emitter and a receiver within said cartridge.

7. A monitor as claimed in claim 6 wherein said clamp assembly is spring pressed for movement into clamping relationship with said cartridge.

* * * * *